United States Patent [19]
Lezdey et al.

[11] Patent Number: 6,124,257
[45] Date of Patent: Sep. 26, 2000

[54] METHOD OF TREATMENT

[76] Inventors: John Lezdey, 2206 Sandra Rd., Voorhees, N.J. 08043; Allan Wachter, 9822 S. Grandview, Tempe, Ariz. 85284

[21] Appl. No.: 09/201,608

[22] Filed: Nov. 30, 1998

Related U.S. Application Data

[63] Continuation-in-part of application No. 08/922,120, Aug. 28, 1997, abandoned.

[51] Int. Cl.[7] .......................... A61K 38/00; A61K 38/28; A61K 38/48

[52] U.S. Cl. .................. 514/2; 514/6; 514/8; 514/12; 514/21; 530/303; 530/397; 424/94.2; 424/94.64

[58] Field of Search ................................ 514/2, 6, 8, 12, 514/21; 530/303, 397; 424/94.2, 94.64

[56] References Cited

PUBLICATIONS

Temmesfeld–Wollbruck et al., *Lung,* vol. 173, No.3, pp. 139–164, 1995.

*Primary Examiner*—Cecilia J. Tsang
*Assistant Examiner*—Abdel A. Mohamed

[57] ABSTRACT

Compositions and methods of treating disease and injuries wherein by sequentially or co-administering pulmonarily a polypeptide effective for the treatment of the injury or disease and a protease inhibitor capable of binding with elastase or cathepsin G.

4 Claims, No Drawings

METHOD OF TREATMENT

RELATED APPLICATION

This application is a continuation-in-part of application Ser. No. 08/922,120 filed Aug. 28, 1997, now abandoned.

FIELD OF THE INVENTION

The present invention relates to an improvement in compositions and methods of treating diseases by inhalation. More particularly, there is provided a method for improving the efficacy of polypeptides which are used in the treatment of diseases by pulmonary administration.

BACKGROUND OF THE INVENTION

The role of neutrophils in ARDS is substantial. The increased accumulation of neutrophils and their activation results in enhanced chemotaxis, release of neutrophil granules and generation of abnormally high levels of oxygen metabolites. Also many inflammatory cascades are activated and many interactions between pathways. Activation of complement, especially complement fragments $C3_a$ and $C5_a$ play a role between the initiating and the actual occurrence of alveolar injury. Cytokine release form mast cells and macrophages results in the presence of tumor necrosis factor (TNF-$\alpha$), elastase, endotoxin, complement $C5_a$, IL-1, cathepsin and platelet activating factors. The presence of these compounds have an adverse effect in the use of polypeptides in the treatment of the underlying disease.

Schecter et al., Biochem Biophys Res Commun 27 (1987) p. 157 described a system of nomenclature to describe the interaction of proteases and their substrates which are widely used in protease literature. The binding site for a polypeptide substrate on a protease is seen as a series of subsites, each subsite interacts with one amino acid residue of the substrate.

Elastase as well as trypsin, chymotrypsin and kallikrein have as their active sites Asp 102, His 57, Ser 195 (chymotrypsin numbering). Elastase is a proteolytic enzyme whose action results in the splitting of a peptide chain into two or more fragments.

Elastase, Cathepsin G and azurocidin from human neutrophils are key components of body inflammatory defense. Perturbations in regulation of their activities lead to many serious pathological states. Besides pulmonary disease, elastase has been found to be involved in psoriasis, sclerosis, scleroderma, angiogenesis (e.g. proliferating hemangiomas). The presence of heparin is of particular significance in angiogenesis as well as histamine and TNF.

Many diseases require the treatment by a polypeptide such as antithrombin III, pulmonary DNase, calcitonin, insulin, and the like. Pulmonary administration of these polypeptides has been shown to be safe and effective. However, smokers inherently have excess elastase present in their lungs. However, the presence of elastase in the lungs either results in interaction with the treating polypeptide or a splitting of the peptide chain so as to cause inaction of the drug or proteolysis.

According to the present invention the sequential or co-administration of a protease inhibitor having an affinity to elastase such as alpha 1-antitrypsin or secretory leucocyte protease inhibitor with a polypeptide such as antithrombin III by a pulmonary would improve the action of the primary drug.

During surgery such as heart surgery there is reperfusion or perfusion injury. Since mast cells are present in and around the heart tissues and there is an inflammatory response, elastase is released. During the surgery it is common practice to provide an anti-clotting factor such as anti-thrombin III. Pulmonary administration has shown to be effective. However, the efficiency of anti-thrombin III is decreased because of the mediators of inflammation such as elastase and/or cathepsin G which are present in the lung.

"Sepsis syndrome" refers to the clinical condition in which patients with infection manifest sever, adverse systemic response, e.g., hypotension, or disseminated intravascular coagulation.

The risks for subsequent development of ARDS is highest in pulmonary aspiration, diffuse intravascular coagulation, severe pneumonia, hypertransfusion, long bone or pelvic fractures, bacteremia, cutaneous burns and cardiopulmonary surgery.

Early intervention of diseases or injuries before ARDS or sepsis or heart attack occurs is critical to a positive outcome and suggests that therapeutic treatment should occur prior to onset of the disease. The combination therapy can therefore reduce the damage by elastase and permit more effective use of the polypeptide used in the treatment.

U.S. Pat. No. 5,093,316 to Lezdey et al., which is incorporated herein by reference, discloses the use of alpha 1-antitrypsin in the treatment of pulmonary diseases where elastase and cathepsin G are involved.

U.S. Pat. No. 4,916,117 to Lezdey et al. discloses the use of alpha 1-antichymotrypsin in the treatment of pulmonary diseases.

SUMMARY OF THE INVENTION

The present invention relates to an improved method for treating a patient having an injury or disease by the pulmonary administration of a polypeptide. The method involves the sequential or co-administration of a protease inhibitor which is capable of binding with elastase or is capable of preventing the release of elastase from mast cells or neutrophils or capable of binding with cathepsin G with a polypeptide which can be inactivated or degraded by elastase or neutrophils or cathepsin G but is effective for treating the underlying disease.

Advantageously, the protease inhibitor is selected form the group consisting of alpha 1-antitrypsin, alpha 1-antichymotrypsin and secretory leucocyte protease inhibitor.

The method is particularly advantageous when the protease inhibitor is administered to improve the efficacy of DNase, antithrombin III. herparin, calctonin, and insulin.

Although alpha 1-antitrypsin can be used alone by pulmonary administration in treatment of reperfusion or perfusion injury, it is particularly advantageous in combination with antithrombin III.

Advantageously the protease inhibitor is one which covalently but irreversibly binds with elastase. The protease inhibitor may be synthetic, natural, or a mutated recombinant protein.

The derivatives or analogs may be used provided their active sites are maintained.

It is therefore an object of the invention to increase the efficiency in treating patients by the pulmonary delivery of polypeptides through the inactivation of elastase which may be present.

DETAILED DESCRIPTION OF THE PREFERRED EMBODIMENTS

In accordance with the present invention a patient who is susceptible to RDS, ARDS or sepsis syndrome through perfusion injury or one who has acquired a disease which is treated by pulmonary administration of a polypeptide which is conventionally used in the treatment is also treated by a sequential or co-administration of a protease inhibitor which is capable of inhibiting the activation of inflammatory cascades and binds with elastase. The protease inhibitor is preferably administered prior to the polypeptide. A suitable inhalation device for administering droplets of the composition in the desired size is the PARI JET INHALER of the Pari Corporation. The compositions can be further administered as a dry powder.

In infants, aerosolization is not easily performed so that it may be necessary to administer the composition directly in the lungs by droplets. During surgery, such as heart surgery, the composition can be administered in combination with antithrombin III to protect against clotting.

Protease inhibitors which are most suitable for use in the invention are the inhibitors which irreversibly bind with neutrophil elastase, for example, alpha 1-antitrypsin, alpha 2-macroglobulin and bronchial mucus inhibitor or those which bind tightly with neutrophil elastase and are slowly removed such as secretory leucocyte protease inhibitor.

Alpha 1-antitrypsin is most preferable of the protease inhibitors because it plays many roles in the treatment of the diseases. Besides being a natural binder of neutrophil elastase, alpha 1-antitrypsin is known to inhibit the degranulation of lung mast cells, inhibit histamine release factors, inhibit the release of (TNF) tumor necrosis factor and inhibit the release of leukotriene $B_4$ from alveolar macrophages and mast cells.

Alpha 1-antichymotrypsin is particularly useful because it is a natural binder of cathepsin-G. Consequently, alpha 1-antichymotrypsin has a multiple role in the treatment of perfusion or reperfusion injury since it deactivates a major oxygen metabolite which causes lung injury and binds with cathepsin which also cause tissue injury.

The preferred protease inhibitors are the native or recombinant human proteins such as bronchial mucus inhibitor, alpha 1-antitrypsin, alpha 2-macroglobulin, alpha 1-antichymotrypsin, and secretory leucocyte protease inhibitor (SLPI) which do not attract antibodies so that they can be in use over long periods of time. A combination of the protease inhibitors is most effective. However, where elastase is a major problem small molecule protease inhibitors which bind with elastase may be use. The low molecular weight inhibitors such as SLPI are preferably used with human deoxyribonuclease I.

The protease inhibitors are particularly useful when administered in combination with a polypeptide such as calcitonin, antithrombin III, DNase, insulin, and heparin.

When use in combination with insulin or heparin the protease inhibitors bind with the elastase or the other protease which cause the splitting of the polyprotein.

The amount of insulin, calcitonin, antithrombin III, DNase, or heparin which is used is the conventional amount that is used in the treatment of a disease, deficiency or as used during surgery which is dependent upon the age, type of disease or injury or surgical procedure which is well established for the specific polypeptide.

The amount of protease inhibitor is also dependent upon the seriousness of the disease and age of patient. For example, when administered by infusion for heart surgery when antithrombin III is being administered, 100–200 mg of antitrypsin, may also be administered either together or separately. It should be understood that the administration of the protease inhibitor can be admixed with the polypeptide and sold in a single unit dose or that the administration is performed separately. It is preferable that the protease inhibitor is administered first so that it may reduce the elastase before the polypeptide is administered. However, since the kinetic energy of the protease inhibitor with elastase is greater than the polypeptide the protease inhibitor-elastase complex is rapidly formed.

The size of the droplets or particles in a dry powder composition should be less than 10 microns, preferably about 1–5 microns.

The following examples further illustrate the practice of this invention, but are not intended to be limiting thereof. It will be appreciated that the selection of actual amounts of specific alpha 1-antitrypsin or other serine protease inhibitors to be administered to any individual patient will fall within the discretion of the attending physician and will be prescribed in a manner commensurate with the appropriate dosages will depend on the patient's age, weight, sex, stage of disease and like factors uniquely within the purview of the attending physician.

EXAMPLE I

To evaluate its potential for inhibiting neutrophil elastase in airways, a study of aerosolized DNase (sold by Genentech) and Prolastin of Bayer was performed using 100 mg of PROLASTIN and 2.5 mg rh DNase delivered by PARI LL nebulizer BID in droplets less than 10 microns. Patients with FEV>60% of predicted were studied. They were not stratified by pre-treatment elastase activity.

EXAMPLE II

In the treatment of cystic fibrosis using DNase (from Genentech) for every ampoule which contain 1mg of DNase, 200 mgs of Alpha 1-antitrypsin in the form of PROLASTIN (Bayer) is administered.

EXAMPLE III

In surgical procedures where antithrombin. III is to be administered, for every 1000 IU units of antithrombin III which is available from Bayer, 200 mg of alpha-1 antitrypsin is administered by inhalation.

EXPERIMENT 1

29 children ranging from 12 to 16 years of age and were suffering from different stages of cystic fibrosis were on a daily regimen of DNase. 15 children were administered 100 mg of alpha 1-antitrypsin by aerosolization. The remaining children were given ibuprofen. Urine samples were taken and tested for desmosine levels. The desmosine levels of all children who were administered alpha 1-antitrypsin had significantly high levels of desmosine. This showed that there was a greater removal of elastase from the lungs than those on ibuprofen.

What is claimed is:

1. In a method for treating a patient with a non-pulmonary disease by the administration of a polypeptide selected from the group consisting of heparin, calcitonin, insulin and anti-thrombin III by pulmonary delivery, the improvement which comprises administering by inhalation a protease inhibitor selected from the group consisting of Alpha 1-antitrypsin and secretory leucocyte protease inhibitor and said polypeptide in an amount sufficient to control the presence of elastase.

2. The method of claim 1 wherein the polypeptide and protease inhibitor are co-administered for treating a non-pulmonary disease.

3. The method of claim 2 wherein said polypeptide is antithrombin III and said protease inhibitor is alpha 1-antitrypsin.

4. The method of claim 2 wherein the disease is diabetes and said polypeptide is insulin and said protease inhibitor is alpha 1-antitrypsin.

* * * * *